United States Patent
Entrekin et al.

(10) Patent No.: US 6,682,484 B1
(45) Date of Patent: Jan. 27, 2004

(54) COMPRESSION PLATE FOR DIAGNOSTIC BREAST IMAGING

(75) Inventors: Robert R. Entrekin, Kirkland, WA (US); Nicholas D. Change, III, Marysville, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/194,766

(22) Filed: Jul. 12, 2002

(51) Int. Cl.$^7$ .................................................. A61B 8/00
(52) U.S. Cl. ........................................ 600/437; 600/459
(58) Field of Search .............................. 600/407–471; 73/625, 626; 128/916, 915, 897; 367/7, 11, 130, 138

(56) References Cited

U.S. PATENT DOCUMENTS

| | | |
|---|---|---|
| 4,434,799 A | 3/1984 | Taenzer |
| 5,664,573 A | 9/1997 | Shmulewitz |
| 5,820,552 A | 10/1998 | Crosby et al. |
| 5,840,022 A | 11/1998 | Richter |
| 5,938,613 A | 8/1999 | Shmulewitz |
| 6,027,457 A | 2/2000 | Shmulewitz |
| 2003/0007598 A1 | 1/2003 | Wang et al. |

FOREIGN PATENT DOCUMENTS

| | | |
|---|---|---|
| DE | 199 26 446 A1 | 1/2000 |
| WO | WO 00/09014 | 2/2000 |

OTHER PUBLICATIONS

Brnic, Z. et al, "Breast Compression and radiation dose in two different mammographic oblique projections: 45 and 60 degrees," Europ. Journ. of Rad., 40(1): 10–5, Oct. 2001 (Abstract only).

Kino, G., "Acoustic Waves: Devices, Imaging, and Analog Signal Processing," Prentice–Hall, division of Simon & Schuster, originally published 1987, corrected edition 2000, pp. 548–562.

NASA, "Deflection and Stress in Preloaded Square Membrane," NASA Tech. Briefs, GSC–13367.

Hueter, T., et al., "Sonics: Techniques for the Use of Sound and Ultrasound in Engineering and Science," John Wiley & Sons, Inc., Fifth Printing, Oct. 1966, pp. 260–261.

Kapur, A., et al., "Fusion of Digital Mammography with Breast Ultrasound—a Phantom Study," Medical Imaging 2000: Physics of Medical Imaging, Proceedings of SPIE vol. 4682 (2002), pp. 526–537.

*Primary Examiner*—Ali M. Imam
(74) *Attorney, Agent, or Firm*—W. Brinton Yorks, Jr.

(57) ABSTRACT

A breast imaging system is described which includes compression plates for retaining a breast during an examination. One of compression plates is formed by a polymeric membrane stretched under tension to provide a rigid but compliant retention surface which is substantially acoustically transparent for the conduct of a sonographic examination. The polymeric membrane may also be substantially radiographically transparent for the conduct of a mammographic examination. The thickness of the membrane is chosen to be a function of one-half of the wavelength of the ultrasonic frequency used for the sonographic examination so as to be substantially transparent to ultrasonic energy at that frequency.

22 Claims, 4 Drawing Sheets

COMPRESSION PLATE FOR DIAGNOSTIC BREAST IMAGING

This invention relates to medical diagnostic imaging systems and, in particular, to diagnostic imaging systems designed for imaging the breast.

The presently preferred imaging modality for breast disease screening is mammography. During a mammographic examination the breast is firmly held between two compression plates while exposed to radiation. Adequate breast compression is fundamental in mammography for optimal image quality. Compression provides breast immobilization which minimizes exposure time and motion blur, and minimizes breast thickness which minimizes geometric blur and absorbed glandular dose. Compression forces can exceed 40 pounds of force for a large breast, so the breast support table is ideally constructed from a material that is both radiographically transparent and mechanically rigid. Epoxy/carbon-fiber composite materials generally satisfy these characteristics.

When a mammogram indicates a suspicious lesion, the next diagnostic step is often to examine the lesion ultrasonically. For this reason it is convenient for the diagnostic instrument to be capable of performing both mammography and sonography. However, in order to combine mammography and sonography into the same scanning device, the breast support table must also be transparent to high-frequency ultrasound. Unfortunately, carbon/epoxy composites are poorly suited for this purpose, since their rigidity creates a large mismatch in sound speed and bulk acoustic impedance compared to human tissue. This mismatch results in high acoustic transmission losses, focusing aberration that degrades spatial resolution, and ring-down artifacts. Conversely, the known polymers with acoustic properties that match human tissue are soft, flexible rubbers or elastomers which readily deflect under large compression forces and are thus poorly suited to act as compression plates. Previous investigators claimed to rely on the intrinsic stiffness of very thin (25 $\mu$mm) polymeric films such as Kapton® polyimide (DuPont, Circleville, Ohio) to provide compression. In practice, it is doubtful that a 25 $\mu$mm film of this (or any known) polymer is sufficiently stiff to resist bending under the large compressive forces needed for screening mammography. Conversely, other investigators have recently studied the use of thick polymer plates (~6 mm) to find the best compromise between acoustic transmission loss and mechanical stiffness. However, the large speed of sound mismatch in a thick plate requires corrections to the beamformer delays to compensate for focusing errors due to refraction. It is thus desirable to provide an acoustic window for the breast support table which simultaneously provides adequate rigidity while maintaining radiographic and acoustic transparency.

In accordance with the principles of the present invention, a compression plate suitable for providing an acoustic and radiographic window for either sonography, mammography, or both is provided by a thin polymer which is mounted under tension. By choosing the appropriate tensile force, the desired rigidity can be provided by a wide range of polymeric membranes. In accordance with a further aspect of the present invention, the thickness of the polymeric membrane is chosen in accordance with the nominal ultrasonic imaging frequency. By choosing a thickness which is a multiple of the ultrasonic wavelength or a fraction thereof such as $\lambda/2$, the membrane can be made virtually completely transmissive at the nominal imaging frequency. The suitability of a wide range of polymeric membranes for the ultrasonic criteria mean that a material with good radiographic transmissivity can be chosen for the acoustic/radiographic window.

Figure 1:
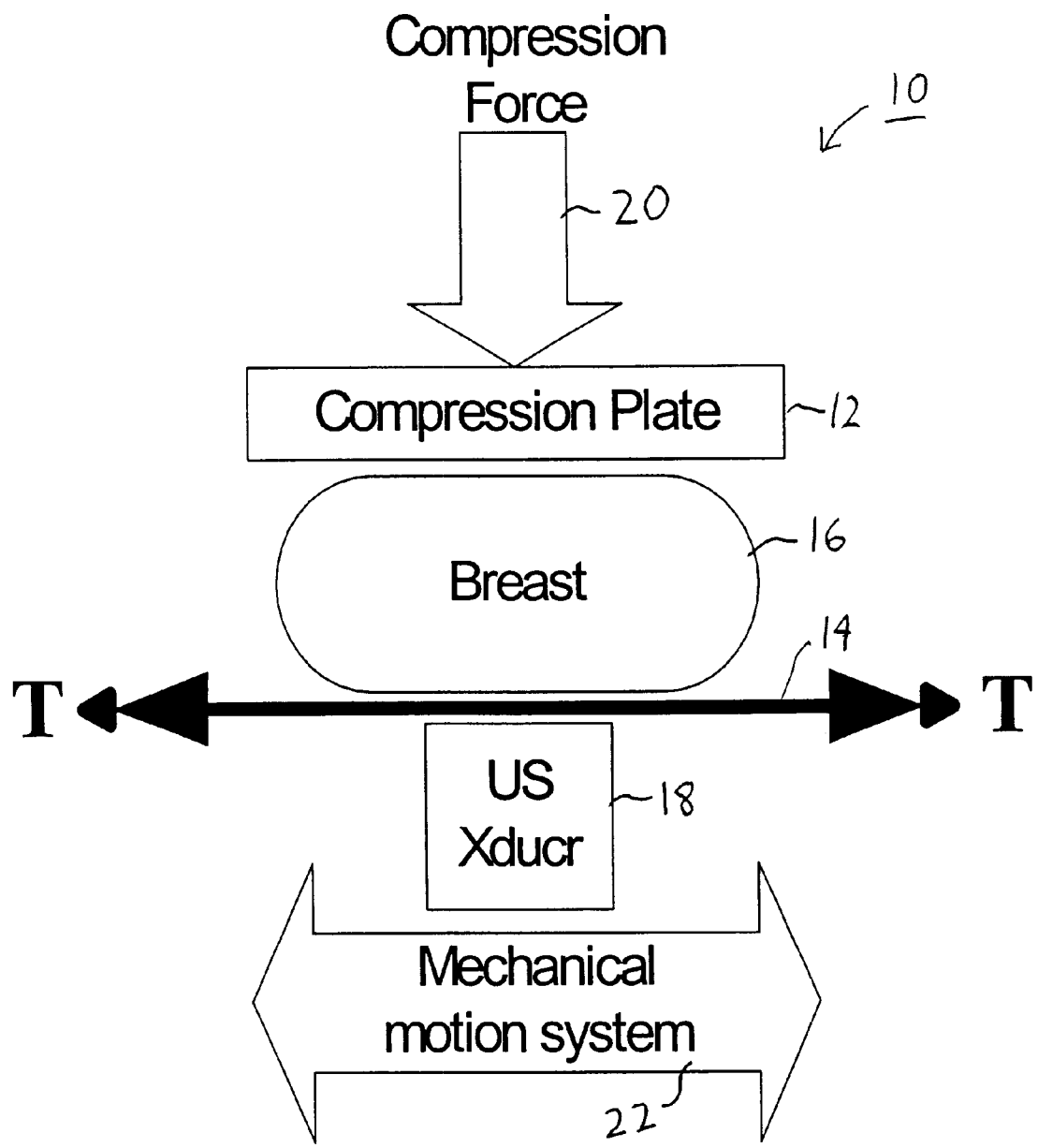
FIG. 1 illustrates a breast scanning system constructed in accordance with the principles of the present invention.

Referring first to FIG. 1, a breast scanning system 10 is schematically illustrated. The breast 16 which is to be scanned is retained between two compression plates 12 and 14. In this embodiment the lower compression plate 14 is fixed in location and the upper compression plate 12 is movable to apply a downward compression force which retains the breast as indicated by the compression force arrow 20. The compressed breast is scanned by an ultrasound transducer 18 located below the lower compression plate 14. The transducer 18 scans the breast by articulation of the transducer in two dimensions by a mechanical motion system 22. In a constructed embodiment the transducer is driven by a motor along a rail in either of two opposite directions in one dimension. The rail is motor driven along two other rails which provides motion in the opposing directions of a second, orthogonal dimension. One dimension would be that of the motion system arrow 22 in FIG. 1, and the other dimension would be into and out of the drawing plane, for instance.

It will be appreciated that the entire system 10 of FIG. 1 could also be constructed in an inverted configuration. That is, the ultrasound transducer could scan the breast from above an upper compression plate and either of the compression plates could move to apply the compressive force.

In accordance with the principles of the present invention, the lower compression plate 14 in the embodiment of FIG. 1 is formed by a thin polymeric sheet which is held under tension in at least one dimension as indicated by the arrows directed in the directions T. By using tension the lower compression plate can be made of a very thin polymeric sheet which is highly transmissive to ultrasound. The tension applied to the sheet provides significant rigidity to the compression plate, a rigidity which, for a thin sheet, can be virtually entirely determined by the amount of tension applied to the sheet. The tension applied can be of any force up to the tensile strength of the polymeric sheet.

In accordance with a further aspect of the present invention, the thickness of the polymeric sheet can be chosen to be highly transmissive to ultrasound. Since the desired rigidity of the compression plate can be set by the tension applied to the sheet, the thickness of the sheet can be chosen in accordance with the wavelength of ultrasound being used. A thickness which is equal to $\lambda/2$ where $\lambda$ is the wavelength of the nominal operating frequency of the transducer will readily pass the ultrasonic energy without reflections or reverberations. As the thickness of the sheet exceeds $\lambda/2$ the problem of reflections and reverberations becomes increasingly greater. However as the thickness of the sheet decreases below the dimension of $\lambda/2$ the problem of reflections and reverberations is minimal. Thus, in a preferred embodiment, the thickness of the sheet is chosen to be approximately $\lambda/2$ or less.

A broadband ultrasound transducer will transmit a range of frequencies. This means that the frequency of interest will, for such transducers, be a nominal frequency for the range used such as the transducer center frequency. The thickness of the sheet can also be chosen in consideration of the receive frequency of interest. For example, for harmonic imaging the received harmonic frequency is the frequency of interest and the thickness can be chosen for the wavelength of the harmonic receive frequency rather than the fundamental transmit frequency. This may mean that reverberations and reflections are generated at the transmit frequency due to a mismatched sheet thickness at the fundamental transmit frequency. But these artifacts can be eliminated by filtering or pulse inversion cancellation on reception as they are outside of the received frequency of interest.

Table I lists a number of candidate materials which are suitable for use as the polymeric sheet in an embodiment of the present invention, together with mechanical and acoustic properties of each material. The tensile strength of the various films range from 4 Kpsi for polymethylpentene to 38 Kpsi for polyethylene naphthalate. Half wavelength ($\lambda/2$) thicknesses range from 73 microns for polyimide at 15 MHz to 286 microns for polyethylene naphthalate at 5 MHz. Other frequencies will yield other preferred thicknesses. The chosen film is stretched to form the acoustic window, applying a tension which preferably does not exceed the tensile strength of the material. With the rigidity of the acoustic window determined by the applied tension, the thickness of the material is chosen to provide good transmissivity of ultrasound. The acoustic transmission will be optimal when the acoustic window thickness is an integer multiple of half of the ultrasound wavelength. This objective is based on the observation that the acoustic energy transmission coefficient T for a thin plate with bulk acoustic impedance $Z_p$ immersed in a medium with impedance $Z_0$ is given [6] by the equation (1):

$$T=\{1+[(m^2-1)/2m]^2\sin^2(2\pi t/\lambda p)\}^{-1} \text{ where } m=Z_p/Z_0 \quad (1)$$

which is premised upon a single ultrasound wavelength (CW conditions) at normal incidence. By setting the material thickness t equal to an integer multiple of $\lambda p/2$, complete transmission (T=1) occurs for a lossless material, regardless of the acoustic impedance mismatch. For a polymer with a speed of 2,500 meters/sec and a frequency of 7.5 MHz, $\lambda p/2$ is equal to 166 $\mu$mm, for instance. Exploiting this relationship will allow the use of polymer films that are mechanically robust, while minimizing acoustic transmission losses. Conversely, these films are still 10 to 30 times thinner than conventional thick windows for breast imaging devices, which will minimize focal aberration due to speed of sound mismatch. Adjusting focal delays in the beamformer could mitigate these aberrations, but this is not expected to be necessary with window materials this thin. Furthermore, at the indicated thicknesses, all of these materials are expected to be substantially radiographically transparent and have negligible effect on x-ray image quality.

Figure 2:
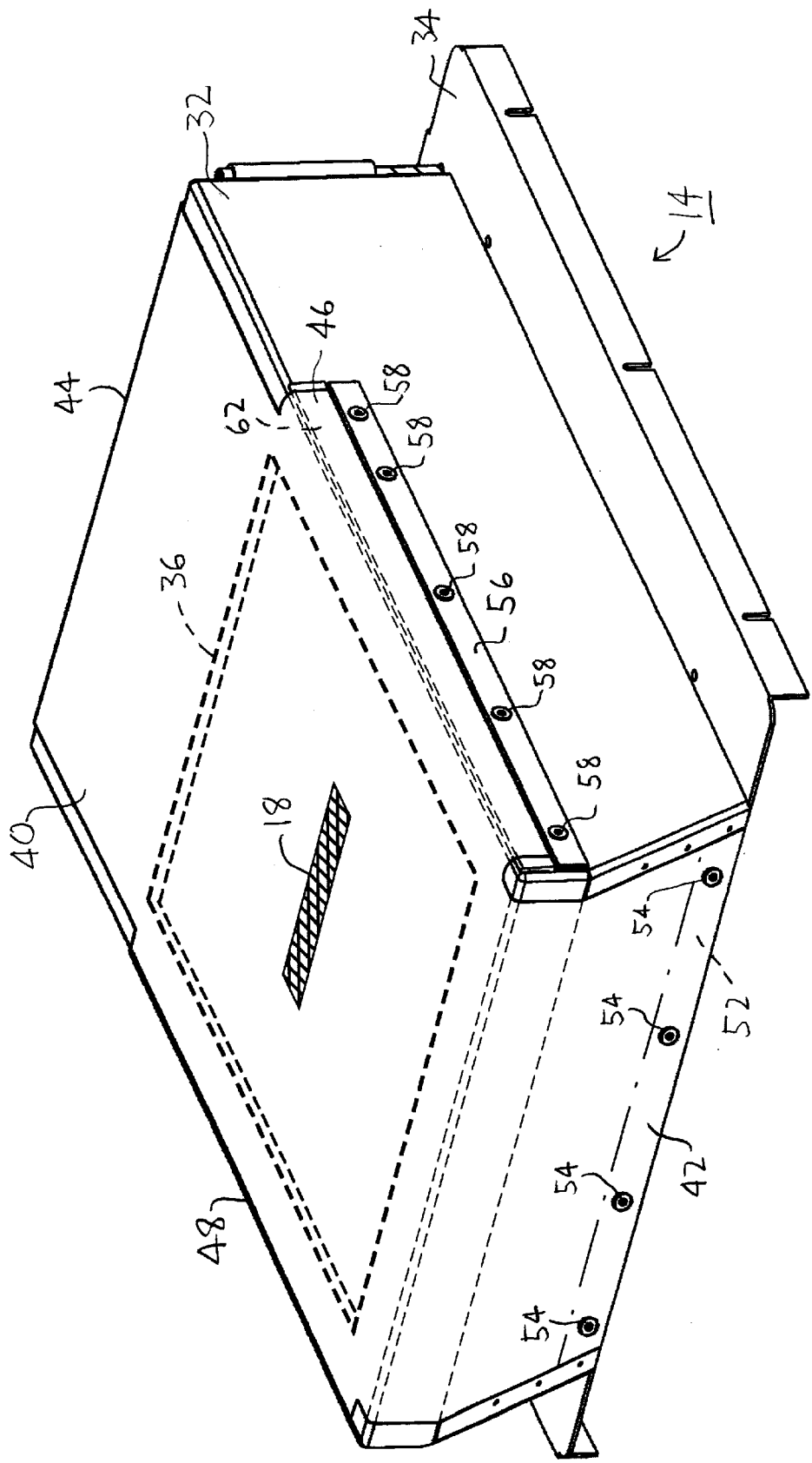
FIGS. 2 and 3 illustrate a breast imaging compression plate in accordance with the principles of the present invention.
Figure 3:
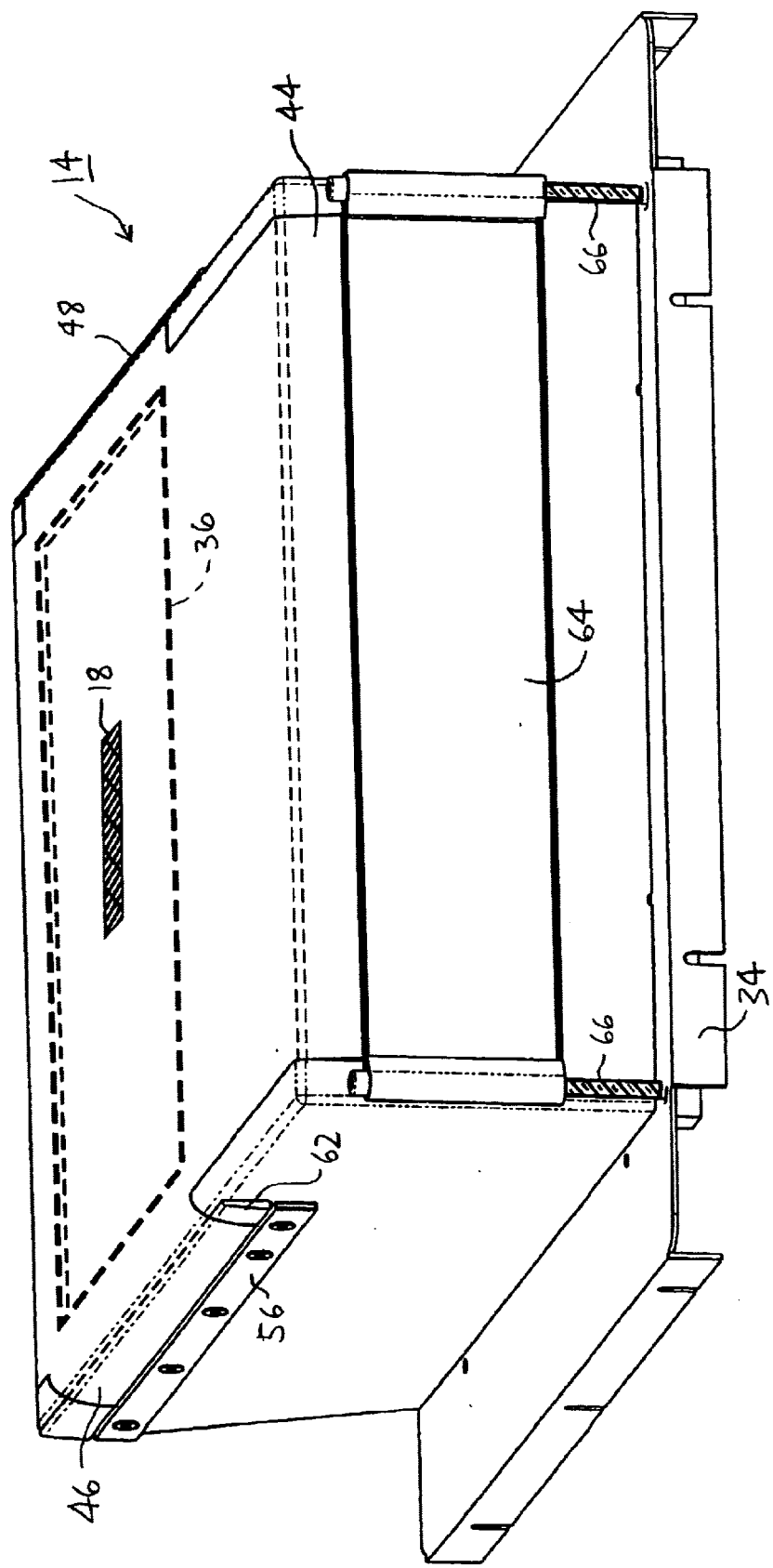

FIGS. 2 and 3 illustrate a compression plate 14 constructed in accordance with the principles of the present invention. The embodiment of these drawings comprises a frame 32 mounted on a baseplate 34. The baseplate is seen to be flanged and perforated so as to mount on a lower part of the breast scanning apparatus (not shown) which contains the control electronics and power supply for the transducer articulation mechanism and a lift mechanism which raises or lowers the compression plate to a height which is comfortable for the patient during the examination. A rectangular opening 36 is formed on the top of the frame 32 and a Mylar membrane 40 is stretched over the opening 36 to form the rigid surface for the compression plate and also the acoustic window for an ultrasound transducer. The ultrasound transducer 18 is located below the membrane 40 and is acoustically coupled to the membrane by an acoustic couplant such as a liquid, a gel, or an oil. In this embodiment the membrane 40 is approximately cross-shaped, with a forward extension 42, a rearward extension 44, and side extensions 46 and 48. The forward extension 42 extends down the front of the frame 32 and underneath the front of the frame where the end of the membrane is wrapped around a front bar 52 located inside the frame. The front bar is held in place by screws 54. At the rear of the frame 32 the rearward extension 44 extends down the back of the frame and is wrapped around a rear bar 64 at the back of the frame (see FIG. 3). The rear bar 64 is mounted on two end screws 66 which can be adjusted to raise and lower the bar rear 64, the screws being threaded into holes in the baseplate 34. As the rear bar is raised or lowered the lateral front-to-back tension of the membrane is decreased or increased correspondingly.

The side extensions 46 and 48 of the membrane 40 are wrapped around side retention bars 56 on either side of the frame, one of which is visible in the drawings. Each side retention bar 56 is fastened to the side of the frame 32 by screws 58 to retain the membrane 40 in a stretched condition across the opening 36. Above each side retention bar 56 is a side tension bar 62 located beneath the membrane 40. Each side tension bar has tabs extending into holes in the side of the frame 32 and the inner surface of each tension bar is contacted by screws threaded through the frame 32. These screws are accessed from inside the frame and as they are screwed through the frame 32 they push the side tension bars outward against the membrane 40 which increases the tension of the membrane across the opening 36.

Figure 6:
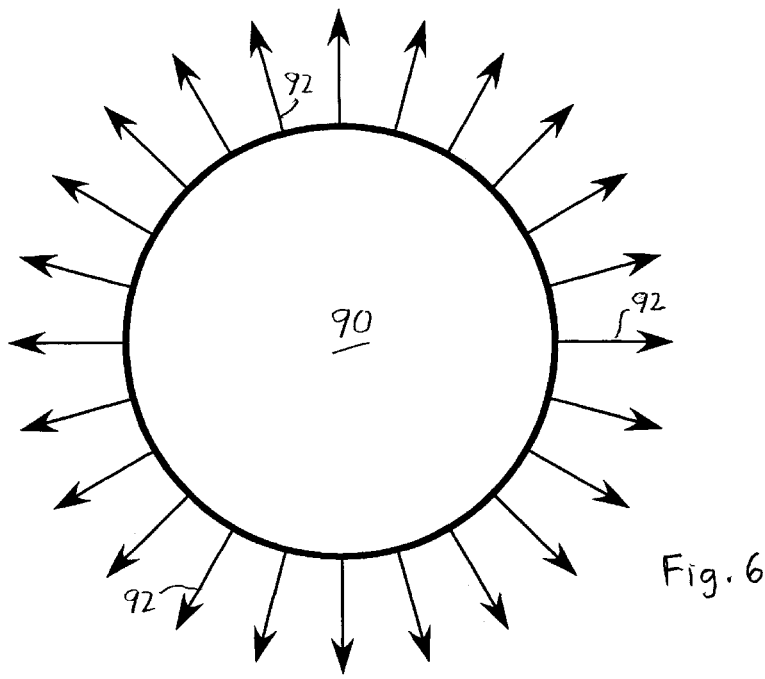
FIGS. 4, 5, and 6 illustrate different ways by which the membrane of an acoustic window of the present invention can be placed under tension.
Figure 4:
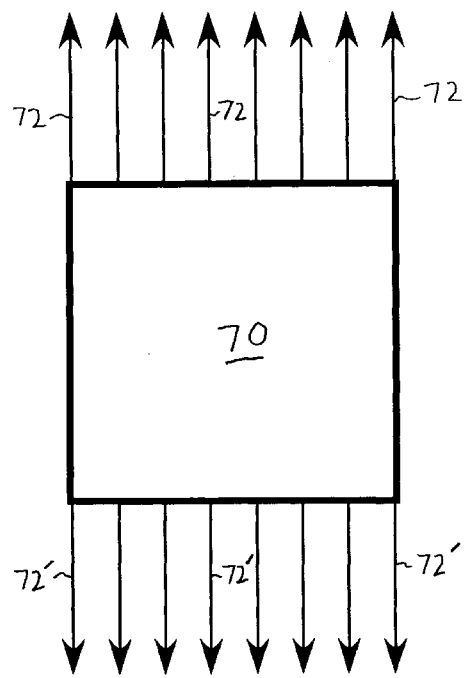
Figure 5:
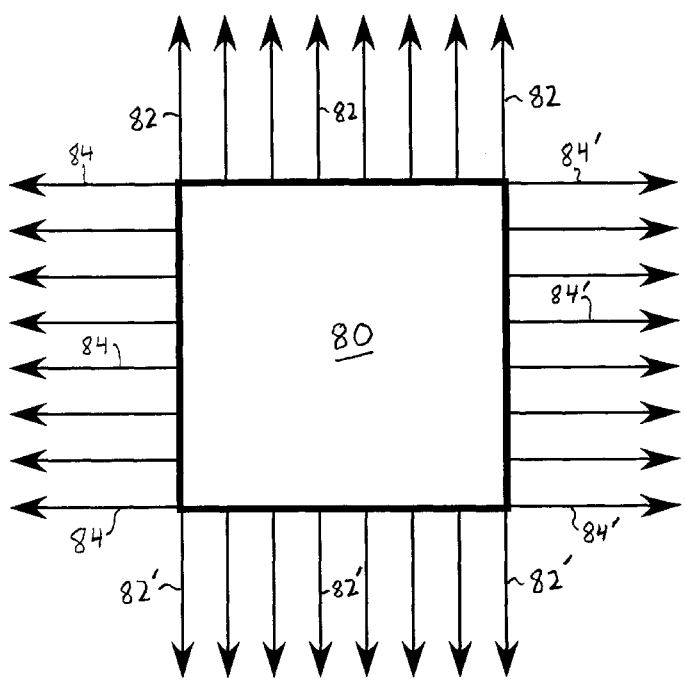

Thus the side bars 62 and the rear bar 64 act to apply controllable bilateral tension to the membrane 40 over the opening 36, the side bars 62 controlling the lateral (side to side) tension force and the rear bar 64 controlling the front to back tension force. The tension of the polymeric sheet 70 of a compression plate of the present invention can be applied unidirectionally as illustrated by arrows 72, 72' in FIG. 4. Alternatively the tension force can be applied bidirectionally to a sheet 80 as indicated by arrows 82, 82' and 84, 84' in FIG. 5 and as applied by the tensioning bars in the embodiment of FIGS. 2 and 3. The tension force can be applied to the sheet radially in the manner of a drumhead as indicated by arrows 92 radially extending from the sheet 90 in FIG. 6.

We have provided a breast imaging compression plate with a mechanically stiff acoustic window which will not rely on the intrinsic bending stiffness of the material. Instead, we pre-stress a polymer membrane by applying tension to create a restoring force that resists deflection, like a drumhead. The stiffness of the acoustic window is thus limited only by the tensile strength of the material, and can be made quite rigid for suitable high-strength polymers such as polyimide, polyester, and others. Calculations indicate, for example, that the maximum deflection of a 166 $\mu$m by 30 cm square polyester film with an edge preload of 15 pounds per inch under a distributed compression load of 40 lbs which may be needed for breast imaging will be about 5 mm. The membrane preferably exhibits a thickness of about $\lambda/2$ or less at an acoustic frequency of interest for good acoustic transmissivity and is preferably radiographically transparent so as to be suitable for x-ray imaging if desired.

TABLE I

| Acoustic Window Material | Tensile Strength Kpsi | Specific Gravity | Speed of Sound, mm/μsec | Acoustic impedance Mrayl | Thickness, microns λ/2 at 5 MHz | Thickness, microns λ/2 at 7.5 MHz | Thickness, microns λ/2 at 15 MHz |
|---|---|---|---|---|---|---|---|
| Polyethylene naphthalate (PEN) Dupont Teonex | 38 | 1.36 | 2.86 | 3.89 | 286 | 191 | 95 |
| Polyethylene terephthalate (PET) Dupont Mylar | 29 to 34 | 1.37 | 2.54 | 3.48 | 254 | 169 | 85 |
| Polyimide (PI) Dupont Kapton | 24 | 1.42 | 2.2 | 3.12 | 220 | 147 | 73 |
| Polyetherimide (PEI) GE Ultem | 14 | 1.27 | 2.41 | 3.06 | 241 | 161 | 80 |
| Polycarbonate (PC) GE Lexan | 8.6 | 1.2 | 2.27 | 2.72 | 227 | 151 | 76 |
| Polyvinylidene Fluoride (PVDF) Elf Attochem Kynar | 7.5 | 1.78 | 2.3 | 4.09 | 230 | 153 | 77 |
| Polymethylpentene (PMP) Mitsui TPX | 4 | 0.83 | 2.22 | 1.84 | 222 | 148 | 74 |

What is claimed is:

1. An ultrasonic breast imaging system comprising:
   a first compression plate;
   a second compression plate opposing the first compression plate comprising a sheet of polymeric material stretched under bi-directional tension by a retention mechanism; and
   an ultrasonic transducer oriented to transmit and receive ultrasonic energy through the sheet of polymeric material,
   wherein the second compression plate provides an acoustic window for the ultrasonic transducer.

2. The ultrasonic breast imaging system of claim 1, wherein one of the compression plates comprises a movable compression plate for retaining a breast under compression between the compression plates.

3. The ultrasonic breast imaging system of claim 2, wherein the second compression plate exhibits a resilience which is a function of the tension applied to the sheet by the retention mechanism.

4. The ultrasonic breast imaging system of claim 3, wherein the second compression plate exhibits a resilience which is a function of the thickness of the polymeric sheet and the tension applied to the sheet by the retention mechanism.

5. The ultrasonic breast imaging system of claim 3, wherein the retention mechanism applies a radial tension force to the sheet of polymeric material.

6. The ultrasonic breast imaging system of claim 3, wherein the polymeric sheet has a thickness which is in the range of 50 to 300 microns.

7. The ultrasonic breast imaging system of claim 3, wherein the retention mechanism retains the polymeric sheet under a tension which does not exceed the material tensile strength.

8. The ultrasonic breast imaging system of claim 1, wherein the second compression plate has a first surface which opposes the first compression plate, and a second surface which is coupled to an ultrasonic transducer for the transmission of ultrasonic energy into the region between the compression plates.

9. The ultrasonic breast imaging system of claim 8, wherein the ultrasonic transducer is coupled to the second surface by an ultrasonic couplant.

10. The ultrasonic breast imaging system of claim 8, wherein the second compression plate comprises a stationary compression plate and the first compression plate comprises a movable compression plate for applying a compressive force to a breast located between the compression plates.

11. The ultrasonic breast imaging system of claim 10, further comprising a scanning mechanism, connected to the ultrasonic transducer which acts to scan ultrasonic beams in different directions into the region between the compression plates.

12. The ultrasonic breast imaging system of claim 11, wherein the scanning mechanism acts to scan ultrasonic beams over a volume in the region between the compression plates.

13. The ultrasonic breast imaging system of; claim 12, wherein the scanning mechanism acts to articulate the ultrasonic transducer over a plane which is substantially parallel to the second surface.

14. The ultrasonic breast imaging system of claim 1, wherein the second compression plate is substantially radiographically transparent.

15. An ultrasonic breast imaging system comprising:
    a first compression plate;
    a second compression plate opposing the first compression plate comprising a sheet of polymeric material stretched under tension by an adjustable retention mechanism; and
    an ultrasonic transducer oriented to transmit and receive ultrasonic energy through the sheet of polymeric material,
    wherein the second compression plate provides an acoustic window for the ultrasonic transducer, and
    wherein the tension applied by the retention mechanism is adjustable.

16. An ultrasonic breast imaging system comprising:
    a first compression plate;
    a second compression plate opposing the first compression plate comprising a sheet of polymeric material exhibiting a thickness which is related to a frequency of interest of an ultrasonic transducer; and
    an ultrasonic transducer oriented to transmit ultrasonic energy through the sheet of polymeric material at a transmit frequency,
    wherein the sheet of polymeric material is substantially transparent to ultrasonic energy at the frequency of interest.

17. The ultrasonic breast imaging system of claim 16, wherein the thickness of the sheet of polymeric material is a function of the wavelength of an ultrasonic wave at the transmit frequency.

18. The ultrasonic breast imaging system of claim 17, wherein the thickness of the sheet of polymeric material is a function of one-half of the wavelength of an ultrasonic wave at the transmit frequency.

19. The ultrasonic breast imaging system of claim 18, wherein the thickness of the sheet of polymeric material is substantially equal to or less than one-half of the wavelength of an ultrasonic wave at the transmit frequency.

20. The ultrasonic breast imaging system of claim 16, wherein the second compression plate is substantially radiographically transparent.

21. An ultrasonic breast imaging system comprising:

a first compression plate;

a second compression plate opposing the first compression plate comprising a sheet of polymeric material exhibiting a thickness in the range of 50 to 300 microns which is related to a frequency of interest of an ultrasonic transducer; and an ultrasonic transducer oriented to transmit ultrasonic energy through the sheet of polymeric material at a transmit frequency, wherein the sheet of polymeric material is substantially transparent to ultrasonic energy at the frequency of interest.

22. The ultrasonic breast imaging system of claim 21, wherein the thickness of the sheet of polymeric material is a function of one-half of the wavelength of an ultrasonic wave at the transmit frequency.

* * * * *